United States Patent
Nzike (10) Patent No.: US 9,861,749 B2
(45) Date of Patent: Jan. 9, 2018

(54) DRIVE MECHANISM FOR DRUG DELIVERY DEVICE

(75) Inventor: Philippe Nzike, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 690 days.

(21) Appl. No.: 13/380,773

(22) PCT Filed: Jun. 23, 2010

(86) PCT No.: PCT/EP2010/058942
§ 371 (c)(1),
(2), (4) Date: Mar. 12, 2012

(87) PCT Pub. No.: WO2010/149717
PCT Pub. Date: Dec. 29, 2010

(65) Prior Publication Data
US 2012/0157931 A1    Jun. 21, 2012

(30) Foreign Application Priority Data

Jun. 25, 2009    (EP) .................................... 09008311

(51) Int. Cl.
*A61M 5/20*    (2006.01)
*A61M 5/315*    (2006.01)
*A61M 5/24*    (2006.01)

(52) U.S. Cl.
CPC ............ *A61M 5/20* (2013.01); *A61M 5/3156* (2013.01); *A61M 5/3158* (2013.01);
(Continued)

(58) Field of Classification Search
CPC .......... A61M 5/31525; A61M 5/31528; A61M 5/31526; A61M 5/3153; A61M 5/31533;
(Continued)

(56) References Cited

U.S. PATENT DOCUMENTS

| 533,575 A | 2/1895 | Wilkens |
|---|---|---|
| 4,446,970 A | 5/1984 | Further |

(Continued)

FOREIGN PATENT DOCUMENTS

| CH | 214738 | 5/1941 |
|---|---|---|
| DE | 3409706 | 7/1985 |

(Continued)

OTHER PUBLICATIONS

European Search Report for EP Application No. 09008311, dated Dec. 10, 2009.
(Continued)

*Primary Examiner* — Nathan R Price
*Assistant Examiner* — Weng Lee
(74) *Attorney, Agent, or Firm* — McDonnell Boehnen Hulbert & Berghoff LLP (57) ABSTRACT

The present disclosure relates to a drug delivery device, in particular pen-type injectors, wherein a number or pre-set doses can be administered. In particular, the present disclosure relates to such drug delivery devices, where a user may activate the dose injection process and wherein the user is still able to control the dose injection process even after a dose injection process has been activated. The process of injecting a dose is supported by some kind of energy storing means as well as by a force to be exerted by a user. Moreover, the disclosure characterizes by a reduced amount of mechanical components.

17 Claims, 6 Drawing Sheets

(52) U.S. Cl.
CPC .... *A61M 5/31551* (2013.01); *A61M 5/31595* (2013.01); *A61M 5/24* (2013.01); *A61M 2005/202* (2013.01); *A61M 2205/581* (2013.01); *A61M 2205/582* (2013.01)

(58) Field of Classification Search
CPC ............ A61M 5/3155; A61M 5/31578; A61M 5/31585
USPC .................................. 604/208, 207, 209–211
See application file for complete search history.

(56) References Cited

U.S. PATENT DOCUMENTS

| | | | |
|---|---|---|---|
| 4,973,318 A * | 11/1990 | Holm et al. | 604/208 |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,599,314 A * | 2/1997 | Neill | A61M 5/31555 222/391 |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,241,709 B1 * | 6/2001 | Bechtold et al. | 604/207 |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,740,618 B2 * | 6/2010 | Markussen | 604/208 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0163104 A1 | 7/2006 | Suzuki et al. | |
| 2007/0088290 A1 | 4/2007 | Heiniger et al. | |
| 2007/0093761 A1 * | 4/2007 | Veasey | A61M 5/24 604/207 |
| 2009/0275916 A1 | 11/2009 | Harms et al. | |

FOREIGN PATENT DOCUMENTS

| | | |
|---|---|---|
| DE | 9202429 | 6/1992 |
| EP | 0937471 | 8/1999 |
| EP | 0937476 | 8/1999 |
| WO | 94/22507 | 10/1994 |
| WO | 99/38554 | 8/1999 |
| WO | 01/10484 | 2/2001 |
| WO | 2005/067390 | 7/2005 |
| WO | 2006/014882 | 2/2006 |
| WO | 2006/039930 | 4/2006 |
| WO | 2006/045526 | 5/2006 |
| WO | 2007/017052 | 2/2007 |
| WO | 2007/017053 | 2/2007 |

OTHER PUBLICATIONS

International Search Report and Written Opinion for International App. No. PCT/EP2010/058942, dated Oct. 11, 2010.
International Preliminary Report on Patentability for International App. No. PCT/EP2010/058942, dated Jan. 4, 2012.

* cited by examiner

DRIVE MECHANISM FOR DRUG DELIVERY DEVICE

CROSS REFERENCE TO RELATED APPLICATIONS

The present application is a U.S. National Phase Application pursuant to 35 U.S.C. §371 of International Application No. PCT/EP2010/058942 filed Jun. 23, 2010, which claims priority to _European Patent Application No. 09008311.4 filed on _Jun. 25, 2009. The entire disclosure contents of these applications are herewith incorporated by reference into the present application.

FIELD OF INVENTION

The present disclosure relates to drive mechanisms suitable for use in drug delivery devices, in particular pen-type injectors, wherein a number of pre-set or user-selectable doses of a medicinal product can be administered. In particular, the present disclosure relates to drug delivery devices, wherein a user may individually select a dose and may activate the drug delivery device.

BACKGROUND

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where medicinal product is administered on an irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting or selecting must be easy and unambiguous. Where the device is to be disposable rather than reusable, the device should be cheap to manufacture and easy to dispose (preferably being suitable for recycling). To meet these requirements, the number of parts required to assemble the device and the number of material types the device is made from should be kept at a minimum.

For instance, US 2007/0088290 A1 discloses a drive device for advancing an advancing element relative to a housing over an entire advancing distance. Here, an ampule is connected to a housing of the drive device and a plunger is connected to the advancing element, such that the tensioning force or pressure force of a spring device is transmitted to the plunger. The plunger in the ampule is advanced toward the outlet, leading to a dispensing of the product contained in the ampule. After the advancing element has been advanced by a partial advancing distance, the spring device is tensioned again, i.e. re-tensioned.

After the device has been actuated, the plunger is driven in longitudinal direction exclusively by the spring element. In this way, the movement of the advancing element or the plunger is totally decoupled from the push button and all other components of the device the user may interact with. Hence, during an advancing motion the user or patient has no possibility to manipulate the dose injection process. In particular, when the dose to be injected comprises a multitude of dosing units, after having actuated the device, the entire preselected amount of medicinal product is automatically dispensed, which may in some cases lead to discomfort.

It is therefore an object of the present invention to provide an improved drug delivery device for dispensing of a medicinal product, for example a device which provides a user-controlled dispensing even during the process of dose dispensing. Further, a drug delivery device having a reduced number of components and being easy to handle may be provided, which device may provide intuitive and unambiguous dose selecting and dose dispensing.

SUMMARY

The present disclosure provides a drug delivery device for dispensing of a medicinal product. The device comprises a housing accommodating a container. The housing may have a distal end and a proximal end. The container comprises the medicinal product. The container has a piston. The drug delivery device further comprises a piston rod. The piston rod is axially guided in the housing and rotationally locked relative to the housing. The piston rod has a distal end to mechanically interact with, in particular to drive, the piston of the container. The drug delivery device further comprises a dose selecting element which is arranged to mechanically interact with, preferably engaged with, the piston rod. The dose selecting element is moveable at least in an axial direction. The dose selecting element may be moveable with respect to the housing and preferably with respect to the piston rod. The dose selecting element may be moveable in a proximal direction, in particular with respect to the housing and preferably with respect to the piston rod. The dose selecting element may be moveable from an initial position to at least one dose selecting position, in particular for selecting a dose of medicinal product which is to be delivered. In the dose selecting position, that dose which may be subsequently dispensed from the device may already be selected. The initial position may be the position the dose selecting element has before the dose selecting process is started. For example, the initial position may be the position the dose selecting element is in after the latest dose dispensing action has been completed or the position it has when the device is in the originally supplied condition.

The distal end of the device or a component thereof may be that end of the device or the component, which is closest to the dispensing end. The proximal end of the device or a component thereof may be that end of the device or the component, which is furthest away from the dispensing end.

The dose selecting position may be a position, starting from which the selected dose may be dispensed, for example when moving the dose selecting element towards or back into the initial position. The dose selecting element may be moved into the initial position when dispensing the dose.

Further, a spring element is preferably provided to interact, e.g. to mechanically interact, with the dose selecting element. Spring element and dose selecting element may interact such that the spring element is tensioned when the dose selecting element is in the at least one dose selecting position. The spring element may be tensioned when it is moved into the at least one dose selecting position. The spring element may be tensioned via interaction of the spring element and the dose selecting element.

The spring element is dimensioned—and preferably arranged—such that it only provides a fraction of a force, which is required to release and/or to displace the piston rod in the distal direction for dispensing of the dose. Hence, the spring element may be adapted to provide only a part of the total force being necessary to displace the piston rod in the distal direction during dispensing of the dose.

In this way, a user keeps control over the drug delivery device even during a spring-supported dispensing of a preselected or preset dose. The dose dispensing displacement of the piston rod is no longer entirely governed by the tensioned spring element even though the spring element provides a fraction, preferably a major fraction, of the force required for advancing the piston rod.

In this way, a kind of semi-automatic dose dispensing displacement of the piston rod is provided. A dose dispensing force which has to be provided by a user of the drug delivery device is reduced compared to devices without such a spring element.

Preferably, the spring element provides a fraction from and including ¼ up to and including ¾ of the force required to release and to displace the piston rod in the distal direction for dispensing the dose. The spring element may provide a fraction of more than ½ of the force required to release and to displace the piston rod in the distal direction for dispensing the dose.

According to an embodiment, the device further comprises an actuating element which is adapted to be at least axially displaced relative to the housing. The actuating element may interact with the dose selecting element. The actuating element may be engaged with the dose selecting element. The actuating element may be movable in the proximal direction, in particular with respect to the housing, for selecting the dose. The actuating element may be movable in the distal direction for dispensing the selected dose. By means of the actuating element a dose dispensing action can be triggered, in particular after that dose was selected. Also, the actuating element preferably serves as a means for displacing the dose selecting element relative to the piston rod during dose selection. The actuation means may be a component of the device which is accessible from outside of the device and provided, for example, to interact with the user, for example to be gripped by the user. The actuating element may be adapted to transfer that fraction of the force to the piston rod which is required for the displacement and/or the release of the piston rod and is not provided by the tensioned spring element. This fraction may be exerted by the user on the actuating element.

The actuating element and the dose selecting element can be two separate components of the drug delivery device. According to one embodiment, the actuating element and the dose selecting element are rigidly coupled with respect to each other. Alternatively, the actuating element and the dose selecting element are integrally formed as a single piece. In this way, the actuating element further serves as dose selecting element and vice versa, the dose selecting element may also serve as actuating element.

In effect, by rigidly coupling the actuating element and the dose selecting element, the internal structure of the drug delivery device can be simplified. Further, the number of mechanical components required for dose selecting and dose dispensing can be advantageously decreased. A unitary construction of dose selecting element and actuating element may require a more sophisticated and costly fabricating method such as compared to the two elements being prefabricated separately from one another.

The dose selecting element and/or the actuating element may be displaced in the distal direction, in particular with respect to the housing, during a dose dispensing displacement. The piston rod may also be displaced in the distal direction during the dose dispensing displacement. Preferably, the piston rod, for example due to its engagement with the dose selecting element, is coupled to the advancing motion of the actuating element during the dose dispensing displacement in the distal direction. The user may now initiate, monitor and control the entire dose dispensing action of the drug delivery device, e.g. by varying the force to be exerted on the actuating element during the dose dispensing action and/or by monitoring the movement of the actuating element which may, when moving, be indicative for the dose dispensing process being still ongoing.

Further, the spring supported dose dispensing displacement in distal direction can be individually manipulated by the user according to the user's preferences. For instance, the speed of the dose dispensing displacement can be intuitively and easily manipulated by the user, simply by varying the force applied on the actuating element during the dose dispensing displacement.

According to an embodiment, the spring element and its spring constant are dimensioned depending on the static and/or dynamic friction forces between the piston and the container, as well as depending on various mechanical components of the drug delivery device.

According to an embodiment, it is intended that the force exertable by the (tensioned) spring element does not exceed the sum of all internal forces—static and/or dynamic forces—, for example friction forces, which act against a dose dispensing displacement of the piston rod and/or its actuation by the actuating element, in particular after the dose was selected, before the dose dispensing displacement is actuated and/or during the dose dispensing displacement. In this way, it is effectively prevented, that after having selected the dose and after having tensioned the spring element, a dose dispensing displacement is self-actuated.

The spring element may be designed such that the provided spring force exceeds the dynamic friction but not the static friction, e.g. the static friction force which has to be overcome in order to actuate the dose dispensing action, of the drug delivery device. Hence, after actuating a dose dispensing displacement, the dose dispensing action may be entirely spring driven. In this configuration, the force exerted by the user is only intended to activate the dose dispensing and to set the mechanical components in motion. Once in motion, movement of the components of the device may be driven by the spring. Accordingly, the spring element may be adapted to overcome the dynamic friction force(s) acting during dose dispensing against the dose dispensing displacement, but not the static friction force(s) acting against the actuation of the dose dispensing displacement via the actuating element, in particular when the dose selecting element is in the dose selecting position.

Alternatively, the spring element may be designed to provide a reduced level of spring force, which is even not adapted to overcome the dynamic friction of the drug delivery device. In this case, during a dose dispensing action, the displacement of the piston rod is spring supported but always requires an additional externally supplied force. In this case, a user may have to permanently provide an additional force in the distal direction. As soon as such a user-exerted force drops below a minimum threshold, the dose dispensing displacement of the piston rod immediately stops.

In another embodiment, in the dose selecting mode of the drug delivery device, preferably for selecting the dose of medicinal product, the dose selecting element and/or the actuating element is intended to be rotated relative to the housing and, preferably, with respect to the piston rod. In the dose dispensing mode, preferably for dispensing the selected dose, it is intended to push the actuating element and/or the dose selecting element in distal direction relative to the housing. Preferably, there is no rotation of the actuating element and/or the dose selecting element in the dose dispensing mode. The piston rod may follow movement of the dose selecting element and the actuating element for dispensing the dose.

Therefore, due to the rigid coupling of the dose selecting element and the actuating element or the unitary construction of those elements, the dose selecting element may be rotationally moved during a dose selecting action and the dose selecting element may be displaced axially, preferably only axially, in the distal direction during dispensing of the dose.

According to a further preferred embodiment, the dose selecting element and the housing comprise mutually corresponding retaining means at the radial circumference of the dose selecting element and at the inner surface of the housing facing towards the dose selecting element. The retaining means may comprise at least one recess, preferably a circumferential recess, and at least one protrusion, preferably a circumferential protrusion, extending in radial direction. The recess may be arranged at the inner surface of the housing whereas the protrusion extending in radial direction may be disposed at the outer surface of the dose selecting element and vice versa.

It is even conceivable, that both, the dose selecting element as well as the housing, comprise retaining means of either type, namely (circumferential) recesses and/or (radially extending) protrusions.

The retaining means of the dose selecting element and the retaining means of the housing may be adapted to mechanically cooperate with each other to retain the dose selecting element at a fixed axial position with respect to the housing. For example, the retaining means of the dose selecting element and the retaining means of the housing may abut and/or engage each other, for this purpose. The dose selecting element may be retained in the at least one dose selecting position via cooperation of the retaining means.

According to an embodiment, the at least one protrusion of the retaining means comprises an elastically deformable material. The at least one protrusion may be elastically deformable. By means of a protrusion of that kind a well-defined static friction force may be achieved when the dose selecting element is in the least one dose selecting position. The protrusion may be disengageable from the corresponding recess via elastic deformation. Additionally or alternatively, the at least one protrusion may be spring biased in radial direction. For instance, a prong-like protrusion may be spring biased in radial direction on the radial circumference of the dose selecting element.

In this way, during a dose selecting action, wherein the dose selecting element is displaced in the proximal direction, the engagement of the protrusion with a corresponding recess, e.g. disposed in the inner wall of the housing, can define the dose selecting position of the dose selecting element. Preferably, the retaining means comprise a multiplicity of equidistant circumferential recesses along the axial direction. The distance between neighbouring recesses may correspond to a dosing unit.

Accordingly, engagement of the retaining means, e.g. of the protrusion engaging the at least one recess, may prevent self-actuation of the dose dispensing action after the dose has been selected. After disengagement the dispensing displacement may be partly or entirely spring driven. In particular, the spring element and the retaining means may be designed to provide a self-acting dose dispensing displacement of the piston rod as soon as the retaining means of the dose selecting element is disengaged from the retaining means of the housing.

According to an embodiment, the spring element comprises a compression or extension spring of helical or coil geometry. The spring element is preferably disposed at least partially around the dose selecting element and/or around the actuating element. In the axial direction, the spring element may be disposed between a radially extending protrusion or rim of the dose selecting element and a proximal portion of the housing. Preferably, the spring element abuts in distal direction against a radially extending rim or shoulder of the actuating element, whereas in proximal direction, the spring element abuts against a radially inwardly extending rim or shoulder of the housing.

According to an embodiment, the dose selecting element is threadedly engaged with the piston rod. Since the piston rod is rotationally locked relative to the housing, by rotating the dose selecting element relative to the housing, the dose selecting element itself is displaced in proximal direction, e.g. at least until the dose selecting position has been reached.

According to an embodiment, the device comprises a plurality of predefined dose selecting positions. The dose selecting element is expediently displaced at least until a first dose selecting position has been reached.

Once the dose selecting element has reached the dose selecting position, in which the spring element is sufficiently biased, the dose dispensing action can be triggered by applying a force onto the dose selecting element, either directly or indirectly, e.g. by pushing the actuating element in distal direction.

According to an embodiment, the spring constant of the spring element is dimensioned such that the force provided by the spring element is less than the sum of static and dynamic (internal) friction forces but, preferably, greater than the sum of all dynamic (internal) friction forces. The dynamic friction forces may be forces acting during dispensing of the dose, e.g. after actuation of the dispensing action. The static friction forces may be forces acting after selecting of the dose and before actuation of the dispensing action.

According to an embodiment, the spring element and the retaining means are designed to provide a self-acting dose dispensing displacement of the piston rod as soon as retaining means are disengaged. In this way, the drug delivery device may provide a kind of semi-automatic dose dispensing displacement of the piston rod.

In such cases, wherein the dose to be dispensed comprises several basic dosing units, the axial displacement of the dose selecting element is preferably determined by the axial distance of several adjacent retaining means, e.g. the distance between adjacently disposed circumferential recesses in the housing. In order to initiate a dose dispensing displacement of the piston rod, the user only has to push the actuating element in distal direction in order to overcome the static friction forces of the drug delivery device. After the piston rod has been set in motion, the dose dispensing displacement of the piston rod may be entirely spring driven until the retaining means mutually engage, e.g. when a first dosing unit has been dispensed.

At this stage, a further dosing unit may be dispensed by repeatedly pressing or pushing the actuating element. The piston rod then further advances in distal direction until a further intermediate dose selecting position has been reached or until the entire preselected dose containing a number of dosing units has been dispensed. Hence, during a dose dispensing displacement of the piston rod, a user control is provided, at least at those positions, where corresponding retaining means mutually engage.

According to an embodiment, the drug delivery device further comprises a coupling means. The coupling means is preferably adapted to prevent the dose selecting element and/or the actuating element from rotating relative to the housing, in particular also with respect to the piston rod, during a dose dispensing displacement in distal direction, in particular a dose dispensing displacement of the actuation element and/or the dose selecting element in the distal direction. Rotation of the dose selecting element and/or of the actuating element with respect to the housing, in particular also with respect to the piston rod, may be allowed during dose selection.

According to an embodiment, at least a part of the coupling means is rotationally locked relative to the housing. The coupling means is further axially displaceable relative to the housing. Preferably, the coupling means is axially moveable (e.g. via a connecting means) together with the actuating or dose selecting element. The coupling means provides a kind of clutch, e.g. a slipping clutch, which allows rotation of the dose selecting element and/or the actuating element relative to the housing, in particular also relative to the piston rod, during a dose selecting action, i.e. when the dose selecting element and/or the actuating element are subject to a proximal displacement.

During dose dispensing, preferably, the clutch provided by the coupling means serves to rotationally lock the actuating element and/or the dose selecting element with respect to the housing and/or with respect to the piston rod. In this way, a rotation of the dose selecting element relative to the piston rod can be impeded during dispensing of a dose. Otherwise, a rotational movement of the dose selecting element relative to the piston rod during a dispensing action could lead to a modification of the selected dose. That is to say, rotational movement of the actuating element and/or the dose selecting element with respect to the piston rod during dose dispense might decrease dose accuracy. Accordingly, by preventing this rotation, dose accuracy may be increased.

The coupling means may further provide a control means for the displacement of the actuating and/or dose selecting element relative to the housing, in particular during dose selection. Hence, the coupling means may provide a kind of ratchet wheel providing an audible and/or tactile feedback, e.g. a clicking. Additionally or alternatively, the coupling means may rotationally secure the actuating element and/or the dose selecting element against the force of the spring element during selecting of the dose.

According to an embodiment, the coupling means cooperates with the actuating element and/or the dose selecting element. The coupling means is particularly adapted to rotationally lock the actuating element and/or dose selecting element, when the actuating element and/or the dose selecting element is displaced in the distal direction, i.e. when a user-provided force is exerted in distal direction on the actuating element and/or the dose selecting element for the purpose of dispensing of a dose.

In an embodiment, the coupling means comprises a toothed ring or a geared ring, which is adapted to engage with a correspondingly toothed inner face or geared inner face of the actuating element and/or the dose selecting element, in particular when dispensing the dose. The toothed inner face of the actuating element and/or the mating surface of a correspondingly toothed ring of the coupling means preferably comprise a saw-tooth profile. In this way, the actuating element and/or dose selecting element is free to be rotationally dialled in a distinct direction, in particular for dose selection. By means of the saw-toothed profile, a rotation of the actuating element and/or the dose selecting element in the other direction is prevented, for example when dispensing the dose.

Preferably, at least a part of the coupling means is spring-biased by a clutch spring with respect to the actuating and/or dose selecting element. A suitable clutch spring element is preferably designed as spring washer. By means of the clutch spring element, which may be disposed in an annular recess of the actuating element together with the toothed ring, the latter can be pre-tensioned against the toothed inner surface of the actuating element. Hence, the clutch spring element is adapted to exert a spring force onto the coupling means, e.g. pointing in proximal direction, in order to press the toothed ring against the toothed inner face of the actuating element.

In this way, in the dose selecting mode, the actuating element and/or the dose selecting element can be rotationally displaced relative to the housing in a given direction. When for the purpose of dispensing a dose a pressure is exerted in distal direction on the actuating element, a (back-) rotation or back dialling of the actuating element is effectively impeded.

According to an embodiment, the coupling means comprises at least one axially extending guiding member, e.g. a guiding pin, to be guided in a corresponding axial guiding groove of the housing. Hence, the guiding member serves to provide a rotational lock of the coupling means relative to the housing but allows for an axial displacement of these components.

Since the coupling means is rotationally locked but axially movable with respect to the housing, also the actuating element and the dose selecting element become rotationally locked with respect to the housing. Pushing the actuating element and relaxation of the spring element lead to a dose dispensing motion of the piston rod in distal direction. The motion of the actuation element may be transferred to the piston rod via the dose selecting element, in particular via the dose selecting element abutting the thread of the piston rod.

The subject matter of the different embodiments described above may, of course, be combined with each other.

BRIEF DESCRIPTION OF THE FIGURES

Without any limitation, the present disclosure will be explained in greater detail below in connection with a preferred embodiment and with reference to the drawings in which.

DETAILED DESCRIPTION

Figure 1:
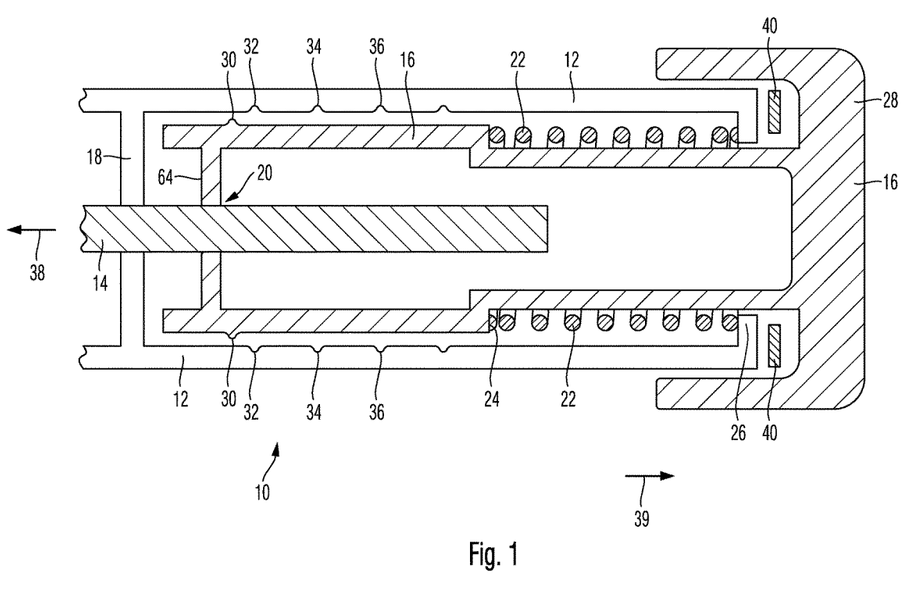
FIG. 1 illustrates the drug delivery device in a simplified cross-sectional view.

According to the simplified illustration of FIG. 1, the drug delivery device 10 comprises a housing 12. The housing 12 has a substantially cylindrical geometry. Near its distal end 38, the housing 12 comprises one or more radially inwardly pointing guiding elements 18, which engage with a threaded piston rod 14. The thread of the piston rod 14 has a series of notches (cf. notches 71 in FIG. 11 that are co-aligned in axial direction and may engage with the inwardly pointing end portion of the guiding elements 18. In this way, the piston rod 14 is rotationally locked relative to the housing 12. Other locking means may be suitable for rotationally locking the piston rod 14 with respect to the housing. The piston rod 14 may be movable with respect to the housing, in particular in the distal direction. The piston rod 14 may be prevented from moving in the proximal direction with respect to the housing. The piston rod 14 may be free to slide in the axial direction with respect to the housing 12.

Figure 11:
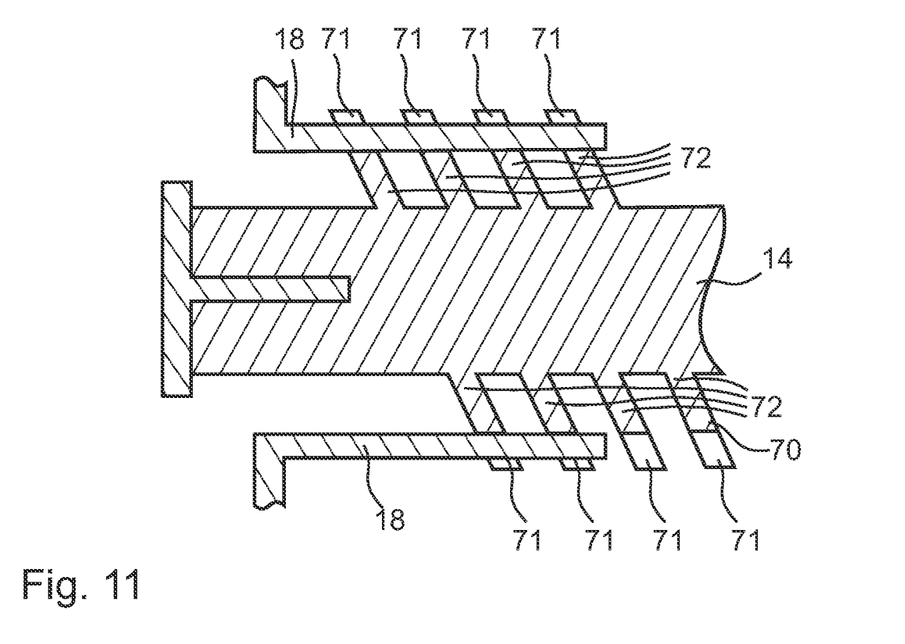
FIG. 11 shows a sectional detail view of the piston rod and the guiding element.

FIG. 11 shows a detail view of the piston rod 14 in the region of the guiding element 18. In FIG. 11, the notches 71 which are co-aligned along the piston rod are explicitly shown. Each turn 72 that is intended to pass guiding means 18 during dispensing operation may comprise such a notch 71. Preferably, each turn of the thread comprises a notch. One guiding element 18 may extend axially and engage one or, preferably, a plurality of notches 71. Engagement of a plurality of notches 71 may enhance locking of the piston rod 14 against rotational movement with respect to the housing 12, and, in particular with respect to guiding elements 18. Guiding elements 18 may, of course, be a part of the housing or separate elements secured thereto. The piston rod 14 may thus be splined to the housing 12. Accordingly, rotation of the piston rod 14 with respect to the housing 12 is prevented, whereas axial movement of the piston rod 14 with respect to the housing 12 is allowed. The notch 71 in the respective turn 72 of thread 70 may extend from the radially outwardly pointing end of this turn further into this turn.

Figure 2:
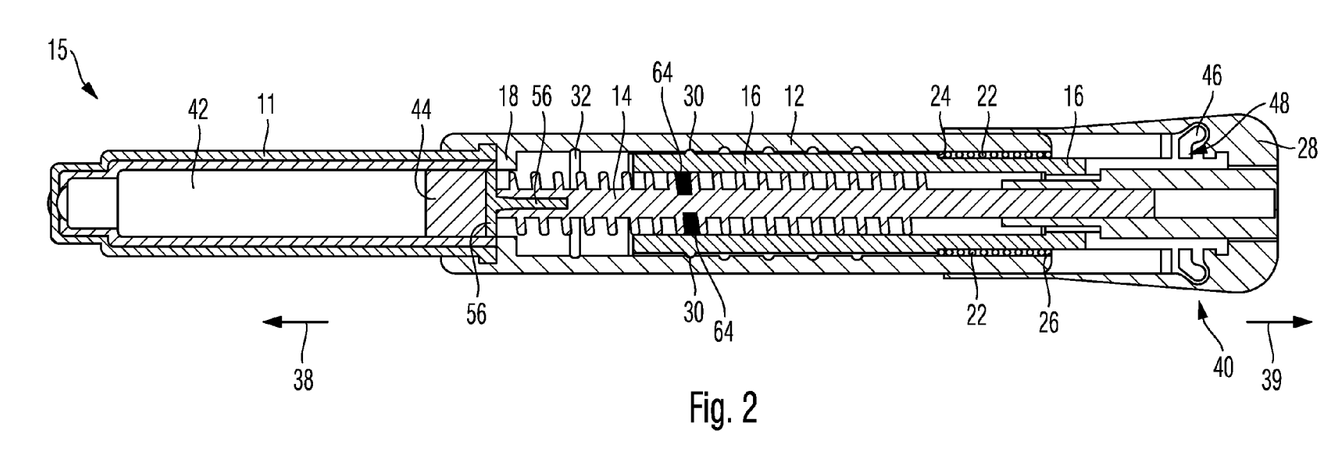
FIG. 2 shows the drug delivery device in a more detailed cross-sectional view, wherein the dose selecting element is in a dose selecting position.
Figure 3:
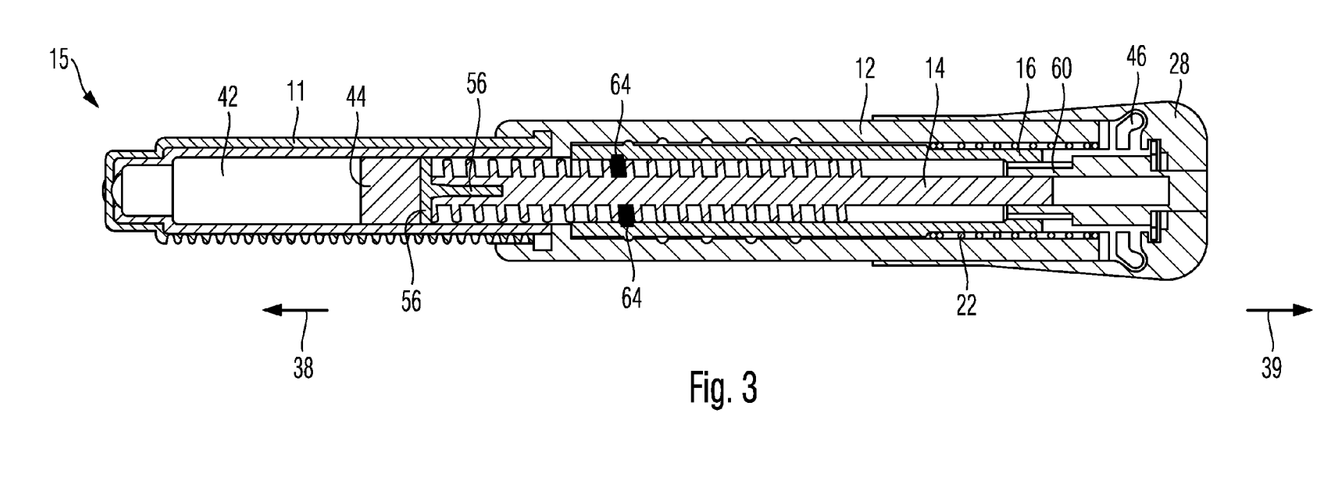
FIG. 3 shows the drug delivery device according to FIG. 2 after injecting of a predefined dose.
Figure 4:
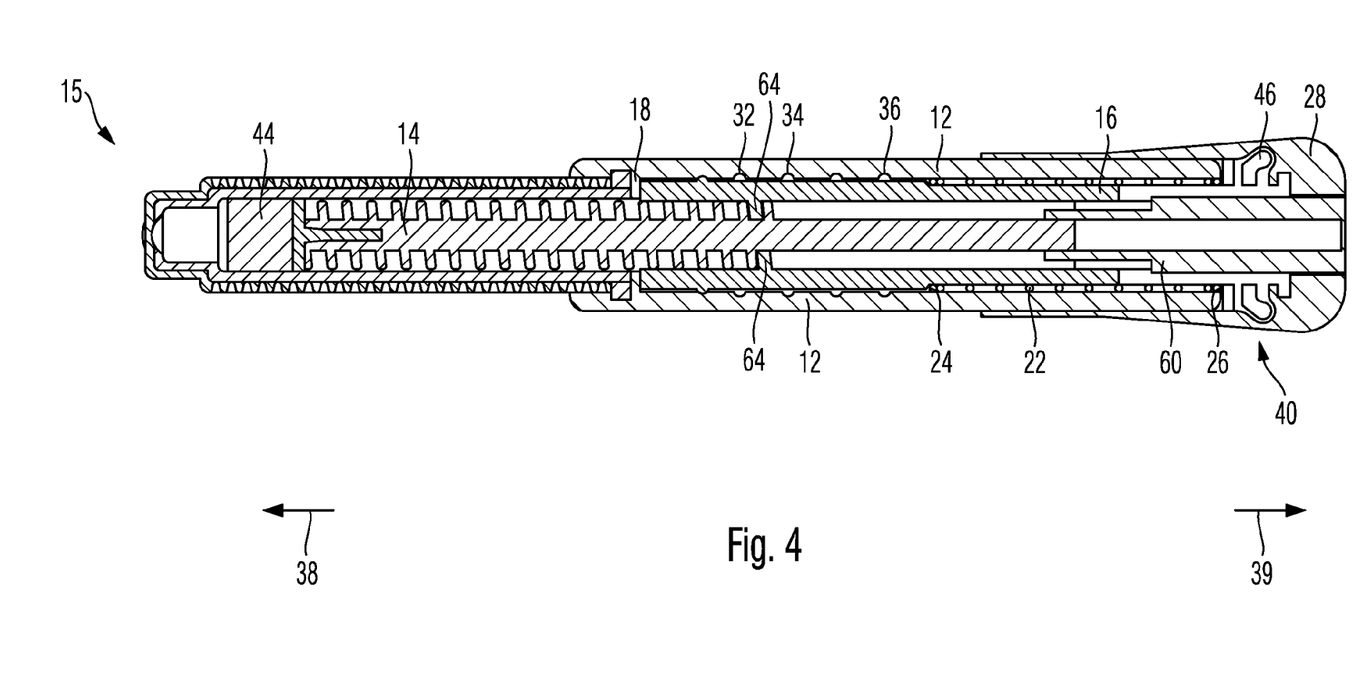
FIG. 4 shows the drug delivery device according to FIGS. 2 and 3, wherein the piston rod has reached its final distal position.
Figure 5:
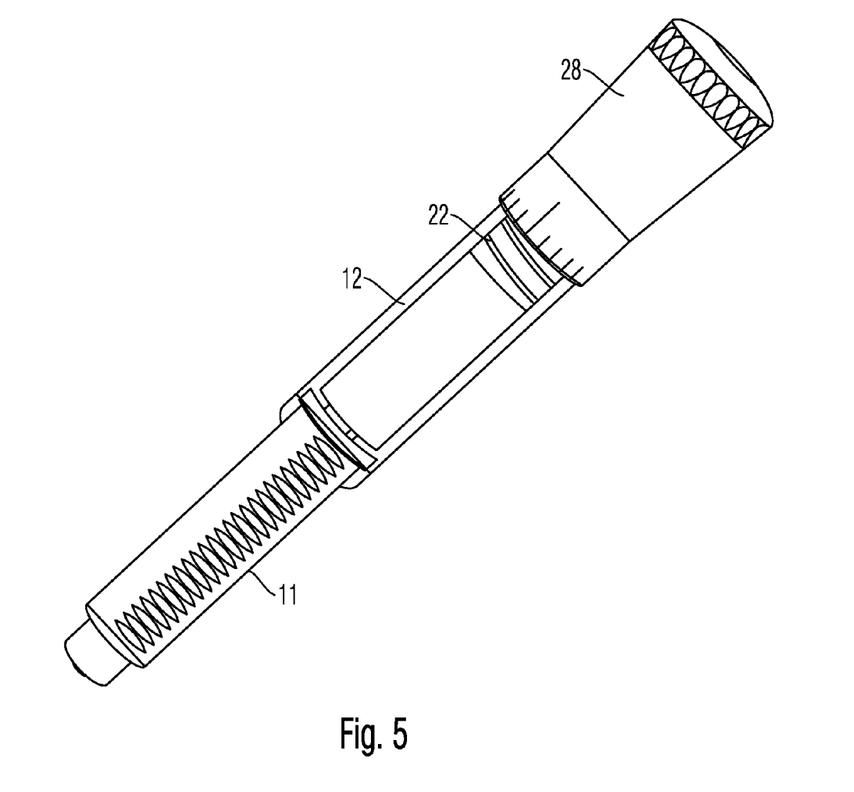
FIG. 5 is a perspective partial cross-sectional illustration shows the entire drug delivery device.

As it is further illustrated in FIGS. 2 through 4, the distal end of the piston rod 14 bears a plunger 56 which abuts a piston 44 of a container 42. The container 42 itself contains a medicinal product to be dispensed. The container is arranged in a container holder 11 which may be a part of the housing 12. The medicinal product may comprise an insulin, e.g. a short-acting or a long-acting insulin, a heparin or growth hormones.

The term "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Returning to FIG. 1, the piston rod 14 is threadedly engaged with a dose selecting element 16. Dose selecting element 16 may be sleeve-like. The dose selecting element 16 comprises one or more inwardly protruding projections 64, which at their radial inward free end preferably match the outer contour of the piston rod 14. In this way, a threaded engagement 20 between the piston rod 14 and the dose selecting element 16 is provided. The projections 64 may be arranged near the distal end of the dose selecting element 16.

The device 15 as illustrated in FIGS. 2 to 4 differs from the simplified illustration of FIG. 1 in that the dose selecting element 16 as depicted in FIG. 1 is no longer designed as single piece, but comprises a sleeve like dose selecting element 16 and an actuating element 28. Dose selecting element 16 and actuating element 28 are rigidly coupled with respect to each other. Hence, the function of the dose selecting element 16 according to FIG. 1 essentially equals the function of the rigidly coupled dose selecting element 16 and the actuating element 28 as illustrated in FIGS. 2 to 4.

By rotating the dose selecting element 16 relative to the housing 12 and hence relative to the piston rod 14, the entire dose selecting element 16 is axially displaced towards the proximal direction 39. A dose of the medicinal product may be selected in this way. The piston rod 14 may be prevented from rotating by mechanical cooperation of the guiding elements 18 with the notches of the thread during selecting and/or dispensing of the dose.

This dose selecting procedure in turn leads to a tensioning of a spring element 22, which is disposed around a proximal portion of the dose selecting element 16. The spring element 22 abuts against a collar or rim 24 of the dose selecting element 16 on the one side and against a radially inwardly pointing collar 26 of the housing 12 on the other side.

The sleeve-like dose selecting element 16 at its outer circumference comprises at least one radially outwardly protruding pin or prong 30, being adapted to engage with a correspondingly designed circumferential recess 32, 34, 36, which may be embodied as groove or notch 32, 34, 36 and which is disposed at the inner surface of the housing 12. The prong 30 and the corresponding grooves or notches 32, 34, 36 form a retaining means in order to keep and to retain the dose selecting element 16 once it has reached a defined dose selecting position.

The distance between adjacent notches 32, 34, 36 determines the amount of medicinal product, which is to be dispensed in a minimal single dose. If for instance the dose selecting element 16 is dialled in such a way, that the protruding prong 30 engages with the notch 32 being arranged closest to the distal end of the drug delivery device, a minimal single dose will be dispensed during a subsequent dose dispensing action. If in a dose selecting procedure the dose selecting element 16 is dialled further, such that the radially outwardly protruding prong 30 engages with the next notch 34, a twofold minimal dose will be dispensed during a successive dose dispensing displacement of the dose selecting element 16 and the piston rod 14.

The dispensing of the dose is finally carried out by pressing or pushing on the dose selecting element 16, e.g. by means of the actuating element 28, which may be rigidly coupled to the dose selecting element 16. Alternatively, dose selecting element 16 and actuating element 28 may be integrally formed as a single piece, as for instance illustrated in FIG. 1. During a dose dispensing action, the coupling means 40 serves to inhibit any rotational or dialling movement of the actuating element 28 or the dose selecting element 16 relative to the housing 12. In this way any axial displacement of the actuating element 28 and the dose selecting element 16 can be unalteredly transferred to a corresponding axial displacement of the piston rod 14 in distal direction 38.

In the case that the user usually has to inject a multiple minimal dose and therefore to dial such a dose, the static and/or dynamic friction forces during advancing of the piston rod 14 in distal direction 38 and the dimensioning of the spring element 22 for example are designed in such a way, that a dose dispensing action always requires that the actuating element 28 is at least initially pushed in distal direction. Once the assembly of piston rod 14, dose selecting element 16 and actuating element 28 has been set in motion, the spring force exerted by the spring element 22 may be sufficient to overcome the sum of all friction forces of the components of the drug delivery device which may slide along one another during dispense. Thus, the dose dispensing displacement of the piston rod 14 may exclusively driven by the spring element 22 until the mutually corresponding retaining means 30, 32, 34, 36, of the dose selecting element 16 and the housing 12 engage for at least temporarily interrupting the dose dispensing action or dose dispensing displacement of the piston rod 14.

When during a dose dispensing action such an intermediate stop position has been reached, a further dose dispensing displacement of the piston rod 14 may be initiated by (repeatedly) pressing the actuating element in the distal direction 38. This may result in dispensing of a second minimal dose and a third minimal dose, depending on the respective dose selecting position of the dose selecting element 16.

The outwardly protruding prongs 30 and/or the 32, 34, 36 notches of the dose selecting element 16 are preferably elastically deformable, such as to allow for a well-defined release and engagement with the housing 12. Additionally or alternatively, these prongs 30 may also be resiliently biased, e.g. by means of spring elements exerting a spring force pointing in radial direction. In any case, the contour and outer geometry of the prongs 30 and the contour and inner geometry of the corresponding notches 32, 34, 36 may be curved, corrugated, in particular convex or concave shaped, thus allowing for a smooth and precise engagement and release.

In the illustrations according to FIGS. 2 through 4, various modes of operation are exemplarily illustrated. In FIG. 2, the drug delivery device 10 is in a dose selecting position. In the situation shown in FIG. 2, the dose has been selected. The spring element 22 has been biased or tensioned by dialling a dose by means of the actuating element 28, thus leading to a corresponding rotation of the dose selecting element 16 relative to the non-rotatable piston rod 14. In this configuration, outwardly protruding prongs 30 of the sleeve-like dose selecting element 16 engage with one of the corresponding but not specifically illustrated notches 32, 34, 36 disposed at the inner wall of the housing 12.

As can further be seen from FIG. 2, the piston rod 14 is in an initial state and the container's piston 44 is located at the proximal end of the container 42. Hence, the container 42 is unused so far.

FIG. 3 illustrates the drug delivery device 10 of FIG. 2 after a dose dispensing displacement of piston rod 14, dose selecting element 16 and actuating element 28 has been conducted. In this configuration, the piston 44 has advanced by a predetermined distance in distal direction 38 and the actuating element 28 as well as the dose selecting element 16 have returned to their initial position relative to the housing 12.

Starting from the configuration of FIG. 3, another dose may be easily selected by rotating the actuating element 28 and hence the dose selecting element 16 with respect to the housing 12 and the piston rod 14. During such a dose selecting procedure, the piston rod 14 is immobile relative to the housing 12, in particular in proximal and/or distal direction, which can be provided by means of some kind of fixing means, for example disposed at the piston rod and/or at the housing 12, e.g. at the radially inwardly protruding guiding elements 18. These fixing means, if arranged at the piston rod, may comprise a saw-toothed profile and they may be resiliently deformable. Preferably, the bevelled flanks of the saw-teeth point in the distal direction, whereas the steep flanks extend substantially in the radial direction.

The fixing means for securing the piston rod against a proximal movement is by no means restricted to the described embodiment. Moreover a manifold of various applicable fixing mechanisms may be applied and implemented here.

FIG. 4 finally illustrates a configuration, where all of the medicinal product has been dispensed from the container 42.

Figure 7:
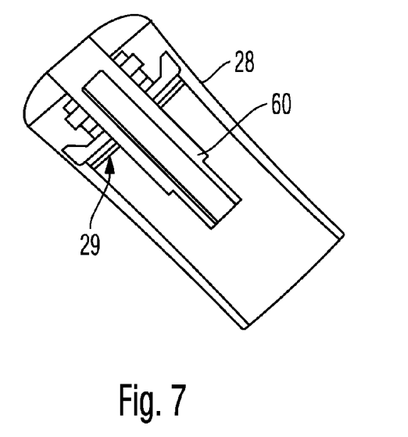
FIG. 7 is a cross-sectional view shows the actuating element.
Figure 8:
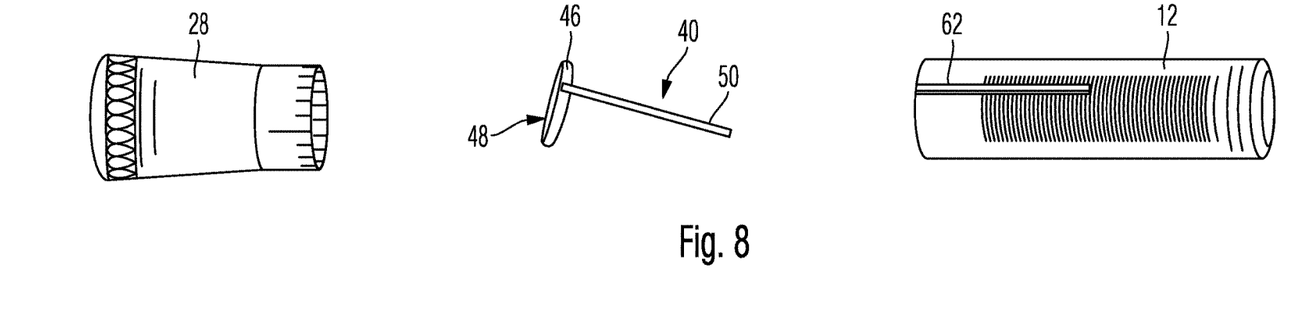
FIG. 8 is a perspective and exploded view depicts the arrangement of actuating element, coupling means and housing.

In the following, the locking function provided by the coupling means 40 is further explained in detail. The coupling means 40 preferably comprises a slit ring 46 which is spring-biased against the inner front end 29 (see FIG. 7) of the actuating element 28. The slit ring 46 further has a guiding pin 50 (see FIG. 8), which provides a rotational locking of the slit ring 46 with respect to the housing 12. Hence, the guiding pin 50 is axially guided in the housing 12, having a corresponding axial channel-like groove 62, as illustrated in FIG. 8.

Figure 6:
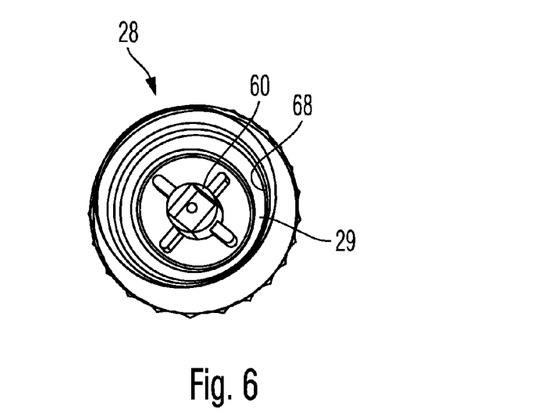
FIG. 6 is a perspective illustration shows the inside of the actuating element.

Further, the slit ring 46 has a slit gear ring 48 (see FIG. 8), which engages with a correspondingly geared inner surface of the inner front end 29 (see FIG. 7) of the actuating element 28. The geared inner surface as well as the slit gear ring 48 comprise mutually corresponding saw-tooth profiles allowing for an unidirectional rotation of the actuating element 28 and/or a corresponding rotation of the dose selecting element 16 in one direction of rotation. In particular, the actuating element 28 and/or the dose selecting element 16 may rotate in this direction with respect to the housing 12 and/or piston rod 14, preferably during dose selecting. In an opposite direction of rotation the actuating element 28, the coupling means 40 and hence the housing 12 are rotationally locked with respect to each other, preferably during dose dispense. Since the slit ring 46 is rotationally locked relative to the housing 12 by its guiding pin 50 and the slit ring 46 is coupled with the geared inner surface, also the actuating element 28 and hence the dose selecting element 16 become rotationally locked relative to the housing 12 and relative to the piston rod 14 when a force is applied to the actuating element 28 in distal direction 38, so that any rotational movement of the various mechanical components of the drug delivery device 10 is impeded during injection. Thus, the actuating element and the dose selecting element may be rotationally locked with respect to the housing The slit ring 46 of the coupling means 40, as illustrated in FIG. 8, is received by a correspondingly designed circumference receptacle 68 of the inner front end 29 of the actuating element 28 (see FIG. 6). Typically, this receptacle 68 allows a coupling/decoupling movement between the slit ring 46 and the actuating element 28. The receptacle 68 further provides an axial linking between the actuating element 28 and the slit ring 46 so that the slit ring 46 follows an axial displacement of the actuating element 28, e.g. when the actuating element 28 is rotated and thereby axially displaced in order to move the dose selecting element 16 into a predefined dose selecting position.

The mutually corresponding teeth of the geared inner surface of the actuating element 28 and the teeth of the slit gear ring 46 further serve as a kind of ratchet and/or slipping clutch giving an audible and/or haptic feedback to the user during the dose selecting procedure.

The actuating or dose dialling element 28 has a hollow shaft 60 (see FIG. 7), which is adapted to receive the proximal portion of the piston rod 14, in particular, when the drug delivery device is in an initial configuration as depicted in FIG. 2.

By means of the shaft 60, a rotational engagement or a rigid coupling between the actuating element 28 and the dose selecting element 16 can be achieved. Typically, the dose selecting element 16 and the actuating element 28 are rotationally locked and they are also rigidly coupled in axial direction.

Figure 9:
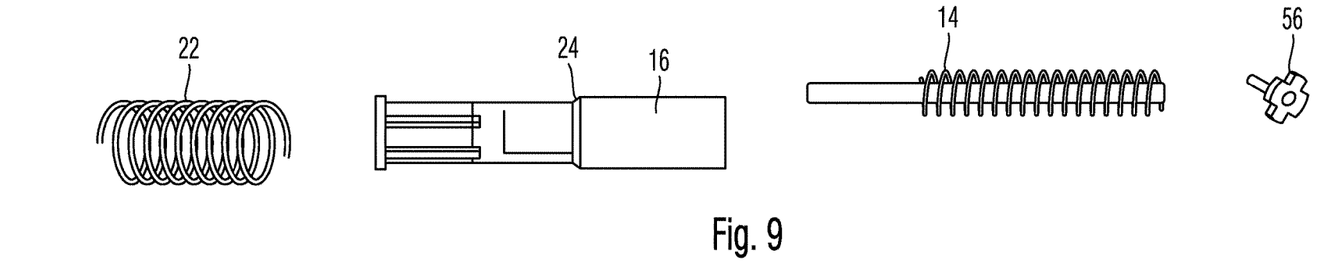
FIG. 9 is another exploded view illustrates the spring element, the dose selecting element and the piston rod.

Further, the proximal end of the dose selecting element 16, as illustrated in FIGS. 8 and 9 as well as the slit ring 46 and gear of the coupling means 40 comprise a slit, which is adapted to maintain the actuating element 28 and the coupling means 40 stable after an assembly. Hence, the respective slit allows for a resilient and temporal deformation during an assembly of the respective component of the drug delivery device 15 during assembling of the device.

Figure 10:
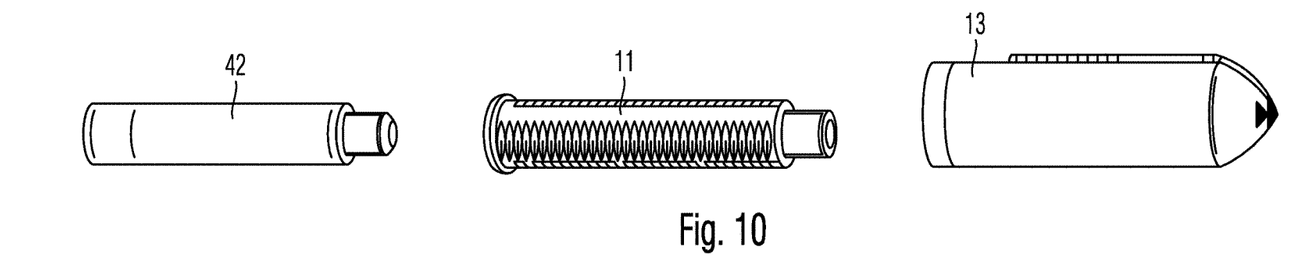
FIG. 10 is another exploded view shows the container, a container housing and a cap to be mounted on the distal end of the drug delivery device.

Finally, in FIG. 10, in an exploded view, the distal portion of the drug delivery device is illustrated. As indicated, the distal portion of the housing 11 is covered by a removable cap 13. In particular, container 42 may be covered by the cap 13.

The invention claimed is:

1. A drug delivery device for dispensing of a medicinal product, comprising:
    a housing having a proximal end and a distal end, the housing accommodating a container at the distal end, the container comprising medicinal product and a piston,
    a dose selecting element positioned within the housing, directly engaged with a non-rotating piston rod and movable in a proximal direction from an initial position to at least one dose selecting position,
    where the piston rod is configured to be axially guided in the housing and to be rotationally locked relative to the housing, the piston rod having a distal end to mechanically interact with the piston of the container,
    an actuating element either rigidly directly coupled to or integrally formed as a single piece with the dose selecting element such that when the actuating element is pushed axially in a distal direction the dose selecting element moves distally and axially with the actuating element from the at least one dose selecting position, whereby the direct engagement of dose selecting element causes the piston rod to follow axial movement of the actuating element and the dose selecting element,
    a spring element biased between the proximal end of the housing and the dose selecting element, wherein the spring element is tensioned in the dose selecting position and a distal end of the spring element abuts a collar on a proximal portion of the dose selecting element and a proximal end of the spring element abuts a collar on the proximal end of the housing,
    wherein the spring element is dimensioned such that it only provides a fraction of a force required to release and to displace the piston rod in the distal direction for dispensing the dose;
    wherein a retaining element is positioned radially on an outer circumference of the dose selecting element, where the retaining element cooperates and engages with at least one of a plurality of cooperating retaining elements positioned radially on an inner surface of the housing and where both the cooperating retaining elements and the retaining element are configured to retain the dose selecting element in the at least one dose selecting position.

2. The device according to claim 1, wherein the actuating element is adapted to be axially displaced relative to the housing.

3. The device according to claim 1, wherein the retaining element comprises at least one circumferential recess or at least one corresponding protrusion extending in a radial direction.

4. The device according to claim 3, wherein the at least one protrusion comprises an elastically deformable material and/or wherein the at least one protrusion is spring biased in the radial direction.

5. The device according to claim 1, wherein the spring element comprises a compression or extension spring of helical and/or coil geometry being disposed around the dose selecting element and/or around the actuating element.

6. The device according to claim 1, wherein the dose selecting element is threadedly engaged with the piston rod.

7. The device according to claim 1, wherein the spring element is configured such that the force provided by the tensioned spring element is smaller than the sum of all internal forces acting against the displacement of the piston rod in the distal direction when the dose selecting element is in the at least one dose selecting position.

8. The device according to claim 1, wherein, when the dose selecting element is in the at least one dose selecting position, the retaining element of the dose selecting element and at least one of the plurality of cooperating retaining elements on the housing are engaged, and the spring element, the retaining element of the dose selecting element and the at least one cooperating retaining element of the housing are designed to provide a self-acting dose dispensing displacement of the piston rod as soon as the retaining element of the dose selecting element is disengaged from the at least one cooperating retaining element of the housing.

9. The device according to claim 1, further comprising a coupling adapted to prevent the dose selecting element from rotating relative to the housing during a dose dispensing displacement of the dose selecting element in the distal direction.

10. The device according to claim 9, wherein at least a part of the coupling is rotationally locked and axially displaceable relative to the housing.

11. The device according to claim 9, wherein the coupling cooperates with the actuating element and/or with the dose selecting element and wherein the coupling is further adapted to rotationally lock the actuating element and/or the dose selecting element during the dose dispensing displacement.

12. The device according to claim 9, wherein the coupling comprises a toothed ring being adapted to engage with a correspondingly toothed inner face of the actuating element and/or a toothed inner face of the dose selecting element.

13. The device according to claim 9, wherein the coupling comprises at least one axially extending guiding pin to be guided in a corresponding groove of the housing.

14. The device according to claim 12, wherein the toothed ring is spring-biased with respect to the actuating element and/or with respect to the dose selecting element.

15. The device according to claim 1, wherein the spring element provides from and including ¼ up to and including ¾ of the force required to release and to displace the piston rod in the distal direction for dispensing the dose.

16. The device according to claim 1, wherein each of the plurality of cooperating retaining elements is configured to act on the retaining element of the dose selecting element in the direction towards the proximal end and in the direction towards the distal end to retain the dose selecting element at a fixed axial position with respect to the housing.

17. A drug delivery device for dispensing of a medicinal product, comprising:
   a housing having a proximal end and a distal end, the housing accommodating a container at the distal end, the container comprising medicinal product and a piston,
   a dose selecting element positioned within the housing, directly engaged with a non-rotating piston rod and movable in a proximal direction from an initial position to at least one dose selecting position,
   where the piston rod is configured to be axially guided in the housing and to be rotationally locked relative to the housing, the piston rod having a distal end to mechanically interact with the piston of the container,
   an actuating element either rigidly directly coupled to or integrally formed as a single piece with the dose selecting element such that when the actuating element is pushed axially in a distal direction the dose selecting element moves distally and axially with the actuating element from the at least one dose selecting position, whereby the direct engagement of dose selecting element causes the piston rod to follow axial movement of the actuating element and the dose selecting element,
   a spring element biased between the proximal end of the housing and the dose selecting element, wherein the spring element is tensioned in the dose selecting position and a distal end of the spring element abuts a collar on a proximal portion of the dose selecting element and a proximal end of the spring element abuts a collar on the proximal end of the housing,
   wherein the spring element is dimensioned such that it only provides a fraction of a force required to release and to displace the piston rod in the distal direction for dispensing the dose;
   wherein a retaining element is positioned radially on an outer circumference of the dose selecting element, where the retaining element cooperates and engages a plurality of cooperating retaining elements positioned radially on an inner surface of the housing in the direction towards the proximal end and in the direction towards the distal end, where both the cooperating retaining elements and the retaining element are configured to retain the dose selecting element at a fixed axial position with respect to the housing.

* * * * *